| United States Patent [19] | [11] 3,969,210 |
| --- | --- |
| Bergson | [45] July 13, 1976 |

[54] APPARATUS FOR WATER DETERMINATION

[76] Inventor: Gustav Bergson, Cedarbrook Hill Apts. 11 Apt. B-117, Wyncote, Pa. 19095

[22] Filed: Apr. 21, 1975

[21] Appl. No.: 569,868

[52] U.S. Cl. ............................ 204/195 W; 73/336.5
[51] Int. Cl.² ............................................ G01N 27/46
[58] Field of Search ...................... 204/1 W, 195 W; 73/336.5

[56] References Cited
UNITED STATES PATENTS

| | | | |
| --- | --- | --- | --- |
| 2,830,945 | 4/1958 | Keidel | 204/195 W |
| 3,232,851 | 2/1966 | Haber et al. | 204/195 W |

*Primary Examiner*—T. Tung
*Attorney, Agent, or Firm*—Jackson, Jackson & Chovanes

[57] ABSTRACT

The invention comprises an improved electrolytic cell of the Keidel type, U.S. Pat. No. 2,830,945, in which the original set of electrodes is replaced by two sets having a ratio of length of not less than 3 to 1 and having independent terminals and independent bodies coupled together. The invention also may comprise potting the element including the longer set of electrodes and leaving the element including the shorter set of electrodes unpotted.

8 Claims, 4 Drawing Figures

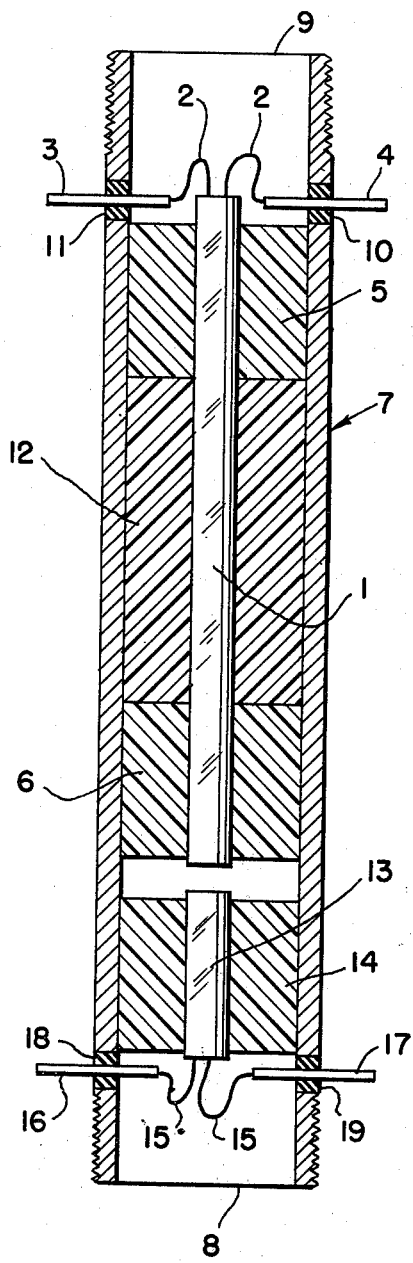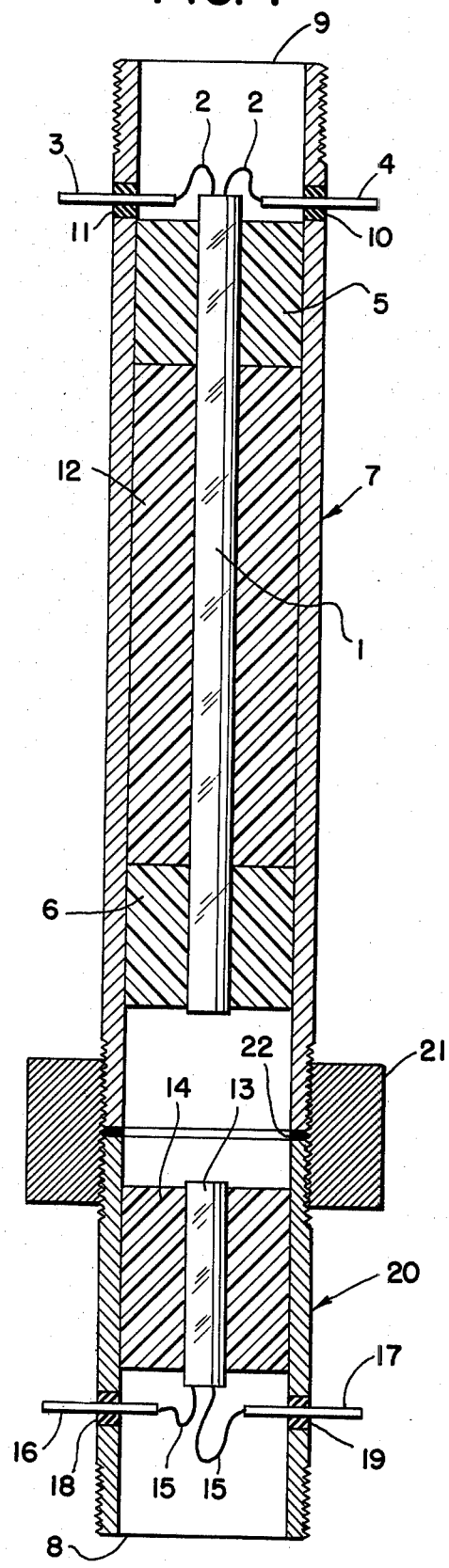

APPARATUS FOR WATER DETERMINATION

DISCLOSURE OF INVENTION

This invention relates to an improved electrolytic cell for use in the determination of water as described in Keidel U.S. Pat. No. 2,830,945 and related apparatus.

PRIOR ART

This invention constitutes an improvement of Keidel U.S. Pat. No. 2,830,945, which is incorporated by reference.

The Keidel Patent shows an electrolytic cell in which two spaced electrodes are, in the preferred embodiment wound in a tube, maintain their spacing, and a material which varies its electrolytic conductivity with variation in water content, such as phosphorus pentoxide, is coated between the electrodes.

THE INVENTION

The improvement comes basically from the observation that in an electrolytic cell such as the Keidel cell, more than half of the water in the entering gas sample whose water content is to be measured is absorbed by the phosphorus pentoxide film which coats the helical pair of wires on the inner wall of the element of the cell, in less than one-fourth of the length of the electrodes. Although the Keidel Patent states that the patented "instruments . . . require only negligible maintenance," this is not the case and the vulnerability of the electrolytic cell particularly adjacent to the input is one cause of this. The replacement requirement of cells is substantial.

This invention separates the inlet portion of the electrodes, so that this portion can be replaced with savings in expense and trouble.

DRAWINGS

In the drawings I show central longitudinal sections of the cell.

FIG. 3 shows the improved form of the invention in elemental form.

FIG. 4 is a section of the improved form of the invention in more sophisticated form.

The drawings of course may be departed from within the spirit of the invention.

DETAILED DESCRIPTION

Figure 1:
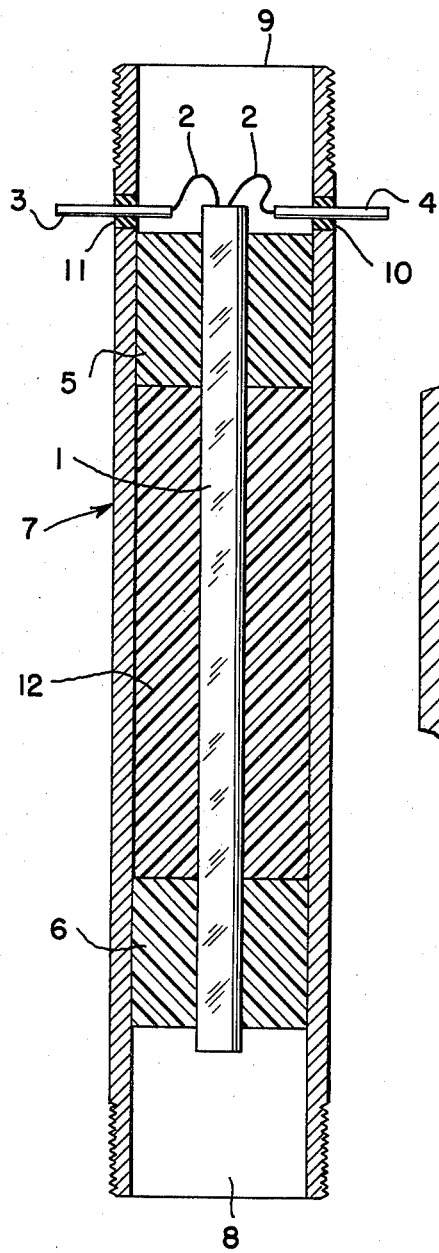
FIG. 1 shows a prior art cell in central longitudinal section.
Figure 2:
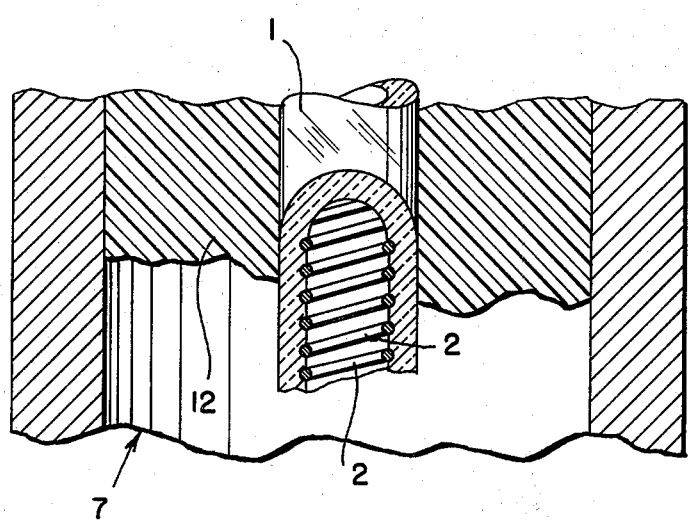
FIG. 2 shows a portion of FIG. 1 in enlarged view.

FIGS. 1 and 2 show a prior art internal core, which is normally about 4 inches in length, with the ends of a helical set of electrodes or wires 2 which is surrounded on the inside of the hollow core 1, thereby forming the element. The electrodes have external terminals 3 and 4 to which the helical pair of spaced wires 2 connect. As in the Keidel patent itself, each particular wire electrode simply comes to an unconnected end at the end away from its particular terminal 3 or 4. The element has end caps 5 and 6 of polytetrafluoroethylene which in the preferred embodiment are suitably one-half inch in length; outside of, and extending between and beyond the end caps, is body 7; and the inlet and outlet ends of the body, into which the gas may be connected to flow into and through the hollow core, are shown at 8 and 9 respectively.

The external terminals 3 and 4 are insulated from the body by insulators 10 and 11. In the usual commercial form the potting material such as epoxy resin 12 fills the space and forms a seal around and between the core 1, the end caps 5 and 6 and the body 7, as shown in the Figure.

In FIGS. 1 and 2 the core may be a glass tube and the spaced wires or electrodes 2 are partially embedded in the inner wall of the glass tube by a process which melts the glass and then allows it to be solidified so that part of the wire protrudes from the glass at the inside. The wires or electrodes in the preferred form are about 0.005 inch in diameter and the spacing between the helical wires is about 0.005 inch.

It will be evident from the Keidel patent incorporated by reference that an electrolytic cell of the Keidel type involves such a cell in which measurement of the amount of water in a give fluid is performed by having electrodes with hygroscopic electrolytically conducting material extending between them. The amount of water absorbed is measured by completely removing that absorbed water by electrolysis of it into hydrogen and oxygen and measuring the quantity of electricity required for this by means of a suitable current-measuring circuit which can be comparatively simple.

FIG. 3 shows an improvement over the prior art of FIGS. 1 and 2 in which there is a new core 1 which may be shortened by approximately ½ inch or so as compared to that of FIG. 1, and there is an additional element having core 13 of ½ inch length with its own separate helical spaced pair of wires 15, which is fitted into the end cap 14 of polytetrafluoroethylene. The external ends of the wires of the additional element are connected to external insulated terminals 16 and 17 insulated from the body at 18 and 19; and the internal ends of the wires simply terminate internally without any connection there to each other or to anything else, just as is likewise true of each of the wires of the new element 1.

It will be noted that the improvement of FIG. 3 thus is made up essentially of two elements, each with its own core including its own electrodes and surrounding structure, including the surrounding portion of body 7. A similar thing will be found to be essentially true in FIG. 4 in which as will be seen, however, the outer structure is somewhat different. The preferred form is shown in FIG. 4 wherein the added core or element 13 is housed in a separate body 20 which is coupled to the body 7 by a coupling 21, suitably threaded, with a gasket of polytetrafluoroethylene 22 serving to prevent leaks when the body extension 20 is tightened against the body 7.

In the cell of the type indicated in FIG. 4, the element or the core extension 13 has a length preferably about a ½ inch and it is nearest to the inlet for the gas 8. The core 1 in the preferable embodiment is about eight times as long as the core extension 13, and in any event should be at least three times as long. Thus core extension 13 will be at most one-third as long as core 1.

When separated the two cell sections can be at substantially different pressures. Thus, the short element can be at an elevated pressure and the long element can be a reduced pressure. Tested under this condition, the water handled by the short cell section at a pressure of 250 psi is substantially greater than the water handled by the long section which is at a pressure of about 15 psi. The short cell sections are easier and more economical to make and it is an advantage to have individual terminals whereby separation of the DC supply resistances can be effected to give lower voltage for the shorter cell section and higher voltage for the long cell section while maintaining full response.

The separation of the cells in the invention also permits measurements in which the shorter section is at an elevated temperature and the longer section is at reduced temperature. Thus, instances are at hand where lowering of sample temperature for complete measurements entails a partial condensation of the sample with carrying over of some water into the condensate. The cell of the present invention contributes to solving these problems. The new cell is adapted for easier and more economical maintenance and improved and more versatile operation, including special applications.

The long and short elements differ from each other not only in their length, but also in the fact that the long element has two polytetrafluoroethylene caps holding the two ends of the long core and potting with epoxy or the like can be used to fill up the interior spaces and preserve the seal. In the short element, the polytetrafluoroethylene holds the core and the electrodes, without need of any potting associated with it.

The shorter element being located at an earlier point in the flowing of gas containing water, the longer element serves as security against having any water evade absorption. Thus, any slightest leakage which occurs around the short element is included in the absorption of the longer element.

The absorption of the short element is far and away greater than would be expected, in view of its short length, and the short element can be readily and cheaply replaced, while the longer element can continue in use during replacement of the shorter element. The short element can be located close to the high pressure part of the system being measured, while the longer element can be located farther away.

In view of my invention and disclosure variations and modifications to meet individual whim or particular need will doubtless become evident to others skilled in the art, to obtain all or part of the benefits of my invention without copying the apparatus shown, and I, therefore, claim all such insofar as they fall within the reasonable spirit and scope of my claims.

Having thus described my invention, what I claim as new and desire to secure by Letters Patent is:

1. An electrolytic cell comprising a first hollow element adapted to pass sample fluid and containing electrodes bridged by a hygroscopic material and a second, separate, hollow element adapted to pass sample fluid and containing electrodes bridged by a hygroscopic material in series of a further point from the standpoint of the passage of the fluid with the first element, the length of the first element being at most one-third of the length of the second element.

2. An electrolytic cell as described in claim 1, in which there is an outer hollow body structure, and there is potting material extending between the exterior of the second element and the outer hollow body structure but no potting material extending between the exterior of the first element and the outer hollow body structure.

3. An electrolytic cell as described in claim 2, in which the outer body structure is made up of one single continuous body.

4. An electrolytic cell of claim 2, in which the two elements are spaced from one another so that the fluid in the one element can be at a substantially different temperature from the fluid in the other element.

5. An electrolytic cell as described in claim 1, in which each of the two elements has its own particular separate outer body, and coupling means acts to join the two bodies together.

6. An electrolytic cell as described in claim 5, in which there is potting extending between the second element and the outer body of the second element but not between the first element and the outer body of the first element.

7. An electrolytic cell of claim 1, in which the electrodes are in each case a pair of helical wires partially embedded in the inner surface of the element.

8. An electrolytic cell of claim 1, in which the two elements are spaced from one another.

* * * * *